United States Patent [19]
Kurono et al.

[11] Patent Number: 5,474,908
[45] Date of Patent: Dec. 12, 1995

[54] METHOD OF ENZYMATICALLY MEASURING HYDROGEN PEROXIDE AND REAGENT THEREFOR

[75] Inventors: Masayasu Kurono; Shizuo Uno; Osamu Takehiro; Kiichi Sawai, all of Aichi, Japan

[73] Assignee: Sanwa Kagaku Kenkyusho Co., Ltd., Aichi, Japan

[21] Appl. No.: 797,011

[22] Filed: Nov. 25, 1991

[30] Foreign Application Priority Data

Nov. 30, 1990 [JP] Japan .................... 2-329652

[51] Int. Cl.$^6$ .............. C12Q 1/28; C12Q 1/26; C12Q 1/30; C12Q 1/00
[52] U.S. Cl. .................. 435/28; 435/25; 435/4; 435/27
[58] Field of Search ............... 435/28, 19, 11, 435/27, 291, 26, 25, 14, 4; 422/56

[56] References Cited

U.S. PATENT DOCUMENTS

| | | | |
|---|---|---|---|
| 4,212,938 | 7/1980 | Gruber et al. | 435/19 |
| 4,587,100 | 5/1986 | Amano et al. | 435/11 |
| 4,578,245 | 3/1986 | Arai et al. | 435/11 |

FOREIGN PATENT DOCUMENTS 59-66899  4/1984  Japan .

OTHER PUBLICATIONS

Ngo et al; "A Sensitive & Versatile Chromogenic Assay for Peroxidase & Peroxidase–Coupled Reactions", Jour. Analytical Biochem; vol. (105) No. 2, pp. 389–397, 1980.
White et al, Prin of Biochem; 6th Edition, Pub. 1978, pp. 419–421.
Saunders et al, "Peroxidase", Pub. 1964, p. 3.

Primary Examiner—Michael G. Wityshyn
Assistant Examiner—Louise N. Leary
Attorney, Agent, or Firm—Nikaido, Marmelstein, Murray & Oram

[57] ABSTRACT

A method of enzymatically measuring hydrogen peroxide by developing a color with use of 3-methyl-2-benzothiazolinoehydrazone as a coupler and in combination with an oxidative color developing reagent with peroxidase, and a reagent therefor is described. Catalase is added to the 3-methyl-2-benzothiazolinonehydrazone reagent as a stabilizer and the reaction is carried out in the presence of ethylenediaminetetraacetic acid or an analogue thereof. The color developing reaction may be carried out in neutral or weak alkali conditions. A reagent is described which comprises a buffer, 3-methyl-2-benzothiazolinohydrazone, and catalase.

4 Claims, 1 Drawing Sheet

A: Containing no catalase
B: Containg catalase of 850 units/ml
C: Blank containg no catalase
D: Blank containing catalase of 850 units/ml A: Containing no catalase
B: Containg catalase of 850 units/ml
C: Blank containg no catalase
D: Blank containing catalase of 850 units/ml

METHOD OF ENZYMATICALLY MEASURING HYDROGEN PEROXIDE AND REAGENT THEREFOR

BACKGROUND OF THE INVENTION

1. Field of the Invention

The present invention relates to a method of enzymatically measuring hydrogen peroxide with high sensitivity and a reagent therefor. The method is utilized in the field of clinical examinations to quantitatively measure various biological substances and enzymes in a body fluid as a sample, through the measurement of hydrogen peroxide.

2. Related art

In the field of clinical examinations, at the present time, the enzymatical measurement of hydrogen peroxide has widely been carried out. For quantitatively measuring a biological substance or enzyme in a sample body fluid such as serum and urine, such an enzymatical measuring method has been developed and actually employed, which comprises steps of generating hydrogen peroxide in the sample with use of an oxidase, and leading into a color developing reaction with use of an oxidative color developing reagent and an oxidase of peroxidase, catalase or the like.

The following illustrates relations between the biological substances to be quantitatively measured by utilizing the generation of hydrogen peroxide and exemplar oxidases to be used therefor.

a) Activity of amylase: α-Glucosidase and glucose oxidase.
b) Activity of guanase: xanthine oxidase and uricase.
c) Glucose: Glucose oxidase.
d) Creatinine: Creatininase and safcosine oxidase.
e) Activity of choline esterase: Choline oxidase.
f) Cholesterol: Cholesterol oxidase.
g) Cholesterol ester: Cholesterol ester hydrogenase and cholesterol oxidase.
h) Neutral fat: Lipase and glycerol oxidase.
i) Activity of transaminase: Pyruvate oxidase.
j) Free (or non-esterified) fatty acids: Acyl-CoA synthetase and Acy-CoA oxidase.
k) Lactic acid: Lactate oxidase.
l) Uric acid: Uricase.
m) Urea: Urease and glutaminate oxidase.
n) Phospholipids: Phospholipase D and choline oxidase.
o) Bilirubin: Billrubin oxidase.

The following illustrates color reaction utilizing the generated hydrogen peroxide.

A) Methods using peroxidase (POD):

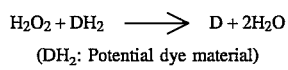

(DH₂: Potential dye material)

B) Methods using catalase: There are methods, for instance, wherein methanol is oxidized with generated hydrogen peroxide to be converted into formaldehyde, and then acetylacetone and an ammonium salt are added to cause a condensation according to the Hantzsch reaction and to develop a color. This method can be shown with reaction formulae, as given below.

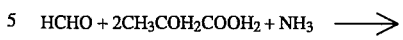

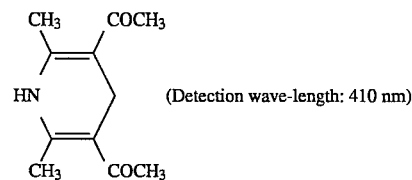

The latter methods using catalase not only require a relatively long operation period of time but also are difficult to apply using an automatical measuring apparatus. Thus, the former methods using POD have widely been employed in the clinical examination field.

Among the color reactions using POD, the method most widely been accepted is that wherein a hydrogen donor is subjected to a condesation reaction with a coupler such as 4-aminoantipyrine (hereinafter referred to as "4-AA"), 3-methyl-2-benzothiazolinonehydrazone (hereinafter referred to as "MBTH") or the like, in the presence of POD, and then the reaction mixture is lead into an oxidative color developing step.

In this case, the following can be used as the hydrogen donor: phenol, 4-chlorophenol, 2,4-dichlorophenol and sulfonated derivatives thereof, 2,4-dibromophenol, 2,6-dichlorophenol, 2,4,6-tribromophenol, 3,5-dichloro-2-hydroxybenzene sulfonic acid, 3-hydroxy-2,4,6-triiodobenzoic acid and the like phenols; N,N-dimethylanillne, N,N-diethylaniline, N-ethyl-N-(2-hydroxyethyl)-m-toluidine, N-ethyl-N-(3-methylphenyl)-N'-acetylethylenediamine, N,N-dimethyl-m-anisidine, N-substituted anilines treated with alkylsulfonic acid or hydroxyalkylsulfonic acid or the like anilines.

Advantages and disadvantages of the conventional methods are as follows.

The methods using 4-AA as the coupler have widely been used, since a detection wave-length for dyes lies at a shorter side, it can be applied in a wide pH range, and reagents show good stability, although a sensitivity thereof is lower than that of the method using MBTH as the coupler. If a reducing substance such as reduced type nicotinamidonucleotide or the like coexists in the reaction system, however, the reducing action is apt to be affected due to such a substance, so that it can happen that color does not appear or tone of the color suppressed.

The methods using MBTH as the coupler are known to be suitable for increased; sensitivity, since a sensitivity is high, detection wave-length lies at higher side, developed color shows good stability, and it is not susceptible to influence of the reducing substance, even if the substance coexists in the reaction system. However, there are disadvantages in that the MBTH reagent per se is not stable, a reagent blank value remarkably changes with the lapse of time, and it can be applied for only in acidic pH range, in practice.

SUMMARY OF THE INVENTION

Therefore, a main object of the invention is to provide such a method for measuring hydrogen peroxide with use of MBTH as the coupler, which has various advantages that the measurement can be carried out in neutral or weak alkali pH range, and shows a sensitivity higher than that of any method using 4-AA as the coupler, in also such a measuring pH range, but does not have the disadvantages of an unstable reagent or an increase in reagent blank value with the lapse of time.

An additional object of the invention is to provide a reagent for carrying out the method, and more particularly an MBTH reagent.

The inventors have energetically studied and investigated under what conditions in the method using MBTH as the coupler for the color developing system to measure hydrogen peroxide, the increase with the lapse of time of reagent blank value occurs and what factor(s) causes such an initialization.

In the first place, they have carried out following experiment. To 10 mM phosphate buffer (pH 7.0), 3.5 U/ml peroxidase, 0.5 mM MBTH, 0.5 mM N-ethyl-N-sulfopropyl-m-anisidine (ADPS), and 0.5 mM EDTA·2 Na (as the case may be) were added, mixed at temperature of 37°, and absorbance (initial absorbance) was measured to check its value on the reagent. Each of the mixed reagents was stored in a refrigerator and the absorbance was measured with a day interval to check an increase of the value. Results are shown in following Table 1.

TABLE 1

| Day elapsed | Containing no EDTA | | Containing EDTA | |
|---|---|---|---|---|
| | Initial absorbance (mABS) | Increase of blank value (mABS) | Initial absorbance (mABS) | Increase of blank value (mABS) |
| 0 | 71 | 33.6 | 44 | 23.5 |
| 2 | 182 | 126.3 | 153 | 24.7 |
| 3 | 295 | 121.4 | 331 | 23.9 |

Through the experiment, two types of phenomena relating to the increase of reagent blank value were observed. One of them is that an absorbance increase with lapse of time, after mixing the color reagents, and the other is that the MBTH solution used increases the initial absorbance, with the lapse of time from the preparation of the solution. The appearance of these phenomena was remarkable in neutral to alkali pH ranges and not noticeable in acidic range (pH 5 or more less), so that as hitherto reported, the method using MBTH is not suitable when measurement is carried out in the neutral or alkali pH range.

Through various studies and investigations, the inventors have estimated that the former phenomena is caused mainly by oxidation due to a metal(s) contained in the reaction solution, although an amount thereof is very small, and that the latter is caused through intrinsic or endogenous hydrogen peroxide that is formed in MBTH solution; in particular, dissolved oxygen in MBTH solution is converted to the oxygen radical by MBTH per se or foreign peroxide and others, and the oxygen radical reacts with a water molecule to generate hydrogen peroxide which increase the initial absorbance, when the MBTH solution is mixed with peroxidase and oxidative color developing reagent (phenols, trinder reagent or the like). Although Jap. Pat. No. Sho 58-899(A) discloses "a stabilized reagents for detecting $H_2O_2$ or $H_2O_2$ doner system and states that an alkali ferrocyanide, chelating agent, and alkali azide are effective as the stabilizing agent, it is not sufficient with only addition of such a compound. Namely, for increasing the sensitivity and stability, it necessary to exclude or suppress both of said two instabilizing factors.

The inventors have continued investigation under the assumption that if the metal(s) contained in the reaction solution can be masked with a chelating agent such as ethylenediaminetetraacetic acid or its analogue and a method for disappearing or suppressing an influence of hydrogen peroxide to be formed from dissolved oxygen in MBTH solution can be established, the increase of reagent blank value may be suppressed to make possible a high sensitive measurement, even though the measurement is carried out in a neutral or alkali pH range. As a result, they have finally found that both the abnormal increase of reagent blank value, namely, absorbance increase with the lapse of time after mixing of MBTH solution and the coloring reagents and the increase of initial absorbance, after the mixing can remarkably be suppressed by carrying out the reaction in the presence of ethylenediamlnetetraacetic acid or its analogue, and by adding catalase to the MBTH solution, and that the addition of the ethylenediamlnetetraacetic acid or its analogue and catalase and the coexistence thereof in reaction system do not adversely effect the color developing system.

Therefore, the enzymatical method according to the invention for measurement of hydrogen peroxide is characterized by using 3-methyl-2-benzothiazolinonehydrazone (MBTH) as a coupler to develop a color in combination with an oxidative color developing reagent and peroxidase, and carrying out a color developing reaction due to oxidational condensation in neutral or weak alkali pH range. The reagent containing 3-methyl-2-benzothiazolinonehydrazone (MBTH) further contains catalase. The color developing reaction is carried out in the presence of an ethylenediaminetetraacetic acid or its analogue. This provides a highly sensitive measurement and attain the main object.

The additional object of the invention can be attained by a reagent comprising a buffer, 3-methyl-2-benzothiazolinonehydrazone (MBTH), and catalase.

For carrying out the method according to the invention, a phenol and trinder reagent known per se can be used as the oxidative color developing reagent. As shown below, a quinone dye will be formed, if the former is used, and in the other case, an indamine dye will be formed.

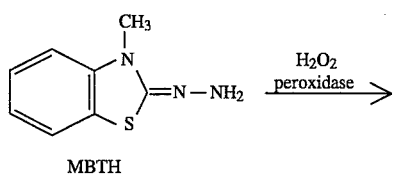

MBTH

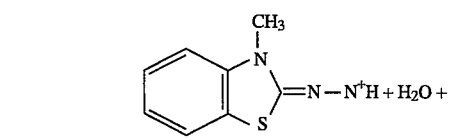

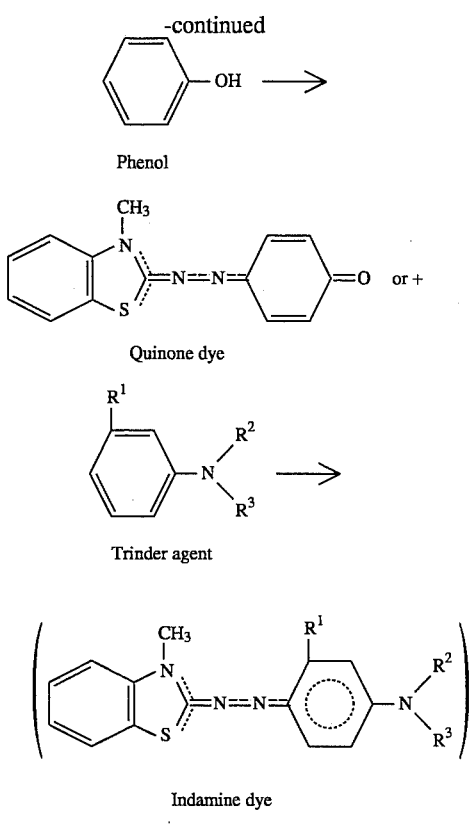

The method according to the invention can be used from a weak acidity pH range to an alkali pH range of about 10, but it is preferable in a pH range of 5.5–9.5.

The amount of catalase in the reagent containing MBTH is at least 10 units per 1 ml of the reagent. As the catalase, which is one of enzymes to decompose hydrogen peroxide, those obtained from an animal, plant or microorganism can be employed for the method according to the invention, if it has been sufficiently purified. As the ethylenediaminetetraacetic acid and its analogues, ethylenediaminetetraacetic acid per se, its sodium, potassium, ammonium, lithium or the like salt, and cyclohexanediamine tetraacetic acid and the like can be used.

BRIEF DESCRIPTION OF DRAWING

The FIGURE is a graph showing a reaction time course, when glucose was measured by a hydrogen peroxide color developing system using glucose oxidase and 3-methyl-2-benzothiazollnonehydrazone, to show a difference between a case where catalase coexists in the measuring system and another case where no catalase is used therein.

DETAILED DESCRIPTION OF PREFERRED EMBODIMENTS

Figure 1:
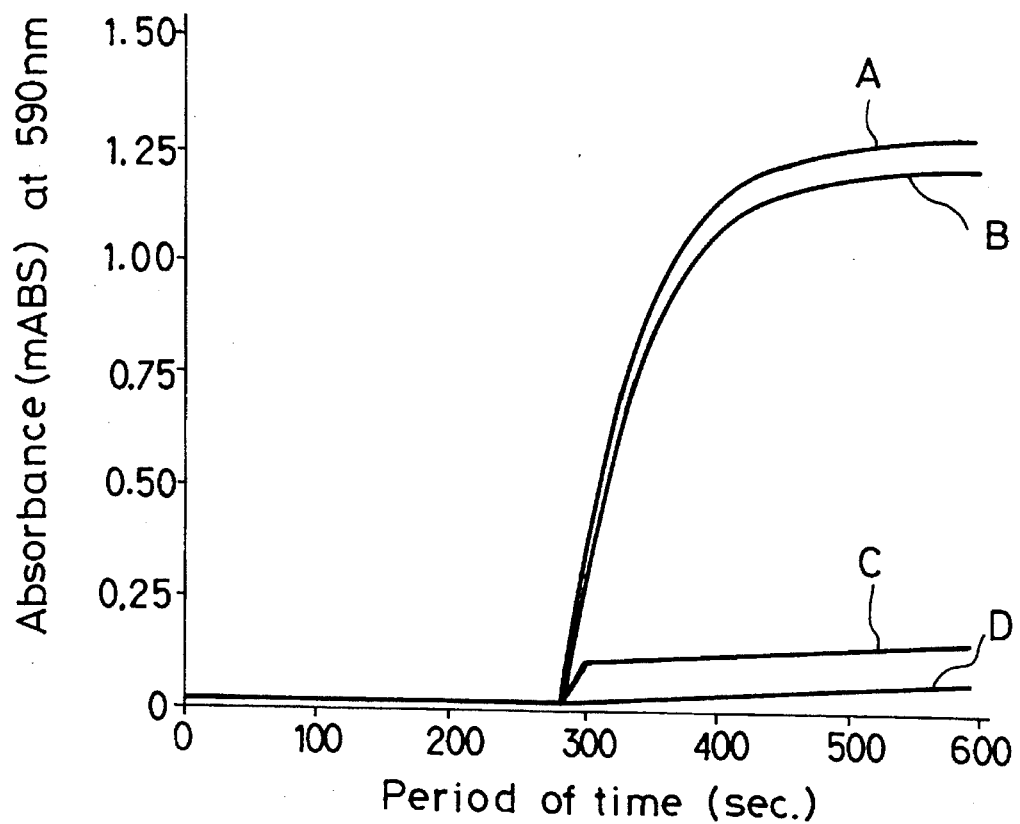

The invention will now be further explained in more detail with reference to Examples.

EXAMPLE 1

1. Reagents
   (a) MBTH reagent
   This reagent was prepared by dissolving 2.2 mg of MBTH and 0–20000 units of catalase in 10 ml of 50 mM phosphate buffer (pH 8.0, containing 0.5 mM EDTA·2 Na).
   (b) ADPS reagent
   This reagent was prepared by dissolving 3.0 mg of ADPS and 70 units of peroxidase in 10 ml of 50 mM phosphate buffer (pH 8.0, containing 0.5 mM EDTA·2 Na).

2. Operations

The MBTH reagent and ADPS reagent were taken in equiamount and mixed. After lapsed 30 seconds at 37° C., an absorbance (initial absorbance) of the mixture was measured at measuring wave-length of 540 nm. Then the mixture was stored at 4° C. under shielding from the light. The mixture was taken out at 2nd, 3rd and 6th day from tile storing, and absorbance (initial absorbance) after lapsed 30 seconds at 37° C. was measured to check the initial absorbance changing with the lapse of time.

3. Results and consideration

Results are shown in following Table 2. As seen in Table 2, which, the MBTH reagent, according to the invention, also contains catalase, an increase of the initial absorbance can significantly be suppressed. The suppressing effect increases as the amount of the catalase increases, but the desired effect can be attained when the catalase is added in the amount of 10 units or more per 1 ml of the MBTH containing reagent. When the catalase was added in the amount of 10 units per 1 ml of the MBTH containing reagent, the increase of initial absorbance after lapsed 6 days was about ⅙, in comparison with that of a MBTH containing reagent with no catalase.

TABLE 2

| Day elasped | Containing amount of catalase (Units/ml) | | | | | |
| --- | --- | --- | --- | --- | --- | --- |
| | 0 | 10 | 20 | 200 | 1000 | 2000 |
| 0 | 34 | 30 | 27 | 21 | 14 | 15 |
| 2 | 131 | 38 | 37 | 20 | 18 | 17 |
| 3 | 160 | 41 | 40 | 18 | 16 | 14 |
| 6 | 235 | 42 | 41 | 20 | 15 | 14 |

(In Table 2, the values are given in mAbs)

EXAMPLE 2

1. Reagents
   (a) First reagent (MBTH reagent containing catalase)
   This reagent was prepared by dissolving 1.1 mg of MBTH and 8500 units of catalase in 10 ml of 50 mM phosphate buffer (pH 7.0, containing 0.5 mM EDTA·2 Na).
   (b) Control reagent (MBTH reagent containing no catalase)
   This reagent was prepared by dissolving 1.1 mg of MBTH in 10 ml of 50 mM phosphate buffer (pH 7.0, containing 0.5 mM EDTA·2 Na).
   (c) Second reagent
   This reagent was prepared by dissolving 3800 units of glucoseoxidase, 700 units of peroxidase and 20 mg of TOOS in 10 ml of 50 mM phosphate buffer (pH 7.0, containing 0.5 mM EDTA·2 Na).
   TOOS: N-Ethyl-N-(2-hydroxy-3-sulfopropyl)-m-toluidine
   (d) Glucose solution
   This solution was prepared by dissolving 40 mg of glucose in 100 ml of refined water.

2. Operations

20 μl of the glucose solution or refined water was mixed with First reagent at 37° C., left to stand for 5 minutes, added 0.2 ml of Second reagent, left to stand for further 5 minutes, and then change of absorbance (reaction time course) was measured at measuring wave-length of 590 nm.

As a control, the change of absorbance was measured as described above, but with use of Control reagent instead of First reagent.

3. Results and consideration

Results are shown in the FIGURE. As shown in the FIGURE, when the control reagent containing no catalase was employed, a sudden increase in absorbance is recognized on the reagent blank just after the addition of the second reagent (Please note the term of "Initial Absorbance" given in this specification designates the absorbance at this increased period of time). It has been theorized that the sudden increase of absorbance was caused by endogenous hydrogen peroxide formed in the reaction solution, as referred to in the preamble part of this specification. The phenomenon of sudden increase of absorbance on the reagent blank did not appear when a reagent containing catalase according to the present invention was used. good reaction time course.

It shall be so concluded from the above that the reduction of accuracy due to increase of reagent blank value which is caused by instability of the reagent can be effectively avoided by the method according to the invention.

What is claimed is:

1. In a highly sensitive method of enzymatically measuring hydrogen peroxide in a color developing reaction using 1) an oxidative color developing reaction reagent, 2) an oxidative coupling reagent consisting essentially of 3-methyl-2-benzothiazolinonehydrazone, and 3) peroxidase, and being carried out in a pH range of weak acid to weak alkali condition, the improvement consisting of:

adding at least about 10 units per 1 ml of oxidative coupling reagent before said oxidative coupling reagent is used in the color developing reaction, and carrying out the color developing reaction in the presence of a compound selected from the group consisting of ethylenediaminetetraacetic acid and analogues thereof.

2. A method as claimed in claim 1, wherein said color developing reaction is carried out in a pH range of 5.5–9.5.

3. A method as claimed in claim 1, wherein said ethylenediaminetetraacetic acid analogue is selected from the group consisting of sodium, ammonium and lithium salts of ethylenediaminetetraacetic acid, and cyclohexanediamine tetraacetic acid.

4. A reagent for a sensitive method of enzymatically measuring hydrogen peroxide, consisting essentially of a buffer, 2-methyl-2-benzothiazolinonehydrazone, and at least about 10 units of catalase per 1 ml of reagent.

\* \* \* \* \*